United States Patent [19]

Schaaf

[11] 4,259,525

[45] Mar. 31, 1981

[54] METHIONINE PROCESS

[75] Inventor: Kurt H. Schaaf, Clearwater, Fla.

[73] Assignee: Diamond Shamrock Corporation, Dallas, Tex.

[21] Appl. No.: 80,198

[22] Filed: Oct. 1, 1979

[51] Int. Cl.$^3$ .................................. C07C 149/247
[52] U.S. Cl. ...................................... 562/559
[58] Field of Search ......................... 562/559

[56] References Cited

U.S. PATENT DOCUMENTS

| | | | |
|---|---|---|---|
| 2,527,366 | 10/1950 | Livak et al. | 562/559 |
| 2,557,913 | 6/1951 | Livak et al. | 562/559 |
| 3,636,098 | 1/1972 | Shima et al. | 562/559 |
| 3,668,221 | 6/1972 | Shima et al. | 562/559 |

OTHER PUBLICATIONS

Pierson et al. Jour. Am. Chem. Soc. 70 1450 (1948).

*Primary Examiner*—John F. Niebling
*Attorney, Agent, or Firm*—Leslie G. Nunn, Jr.

[57] ABSTRACT

Methionine is prepared from 5-(beta-methylmercaptoethyl)-hydantoin at atmospheric pressure by refluxing the hydantoin with a metal hydroxide such as sodium hydroxide, potassium hydroxide, or barium hydroxide and an alkanol having a boiling point of from about 125° C. to about 230° C. at atmospheric pressure, preferably, a water saturated alkanol having a boiling point of from about 125° C. to about 230° C. at atmospheric pressure and thereafter recovering methionine.

10 Claims, No Drawings

METHIONINE PROCESS

BACKGROUND OF THE INVENTION

1. Field of the Invention

This invention relates to methionine manufacture.

2. Description of the Prior Art

U.S. Pat. No. 2,527,366—Livak et al, issued Oct. 24, 1950, describe the preparation of methionine by hydrolyzing 5-(beta-methylmercaptoethyl)-hydantoin with an aqueous solution of barium hydroxide under pressure, e.g., within a bomb or autoclave, at temperatures above 115° C. and usually within the range of from 115° to 210° C. Patentees mention that these conditions of temperature and pressure are not satisfactory for alkaline hydrolyzing agents in general. For instance, ammonium hydroxide and lime when evaluated as hydantoin hydrolyzing agents under similar temperature and pressure conditions, either caused excessive by-product formation and produced the alpha-amino monocarboxylic acid in an unsatisfactorily low yield or formed a badly discolored amino acid which could not be satisfactorily decolorized. Also, barium hydroxide itself, when tested as a hydrolyzing agent at atmospheric pressure, was unsatisfactory, that is, upon boiling a mixture of the hydantoin and aqueous barium hydroxide at atmospheric pressure, hydrolysis occurred very slowly and the yield of alpha-amino monocarboxylic acid was low.

Pierson et al, Jour. Am. Chem. Soc., 70, 1450 (1948) describe a three-step synthesis based on catalyzed addition of methyl mercaptan to acrolein, followed by the Bucherer hydantoin reaction and then by hydrolysis. Methionine was prepared from 17.4 g (0.10 mole) of 5-(beta-methylmercaptoethyl)-hydantoin by refluxing for six hours with a solution of 8.8 g of sodium hydroxide in 75 ml of water contained in a stainless steel flask. An additional 4.4 g of sodium hydroxide was added and refluxing was continued for a total of 24 hours. The reaction mixture was decolorized, neutralized to litmus with concentrated hydrochloric acid and cooled to 5° C. to crystallize. A crude yield of 84.5% was obtained.

U.S. Pat. No. 2,557,913—Livak et al, issued June 19, 1951, disclose that 5-(beta-methylmercaptoethyl)-hydantoin may be hydrolyzed by heating the same together with an aqueous solution of an alkali such as sodium carbonate, potassium carbonate, sodium hydroxide or potassium hydroxide. However, they indicate that hydrolysis with most alkalies results in a low yield or in discoloration. They prefer barium hydroxide and use sufficient water to dissolve the major portion of the barium hydroxide and heat the hydrolysis mixture in a bomb or autoclave at a temperature of from 115° to 210° C. Air is preferably swept from the reactor with nitrogen, steam or other inert gas prior to heating the mixture under pressure since oxygen, if present during the hydrolysis, may cause by-product formation.

SUMMARY OF THE INVENTION

Methionine is prepared by alkaline hydrolysis of 5-(beta-methylmercaptoethyl)-hydantoin at atmospheric pressure by refluxing one mole of the hydantoin with from about one mole to about eight moles of metal hydroxide in a medium containing from about 500 to about 5000 milliliters of an alkanol having a boiling point of from about 125° C. to about 230° C. at atmospheric pressure, preferably, a water saturated alkanol having a boiling point of from about 125° C. to about 230° C. at atmospheric pressure and thereafter recovering methionine. Metal hydroxides such as sodium hydroxide, potassium hydroxide and barium hydroxide may be used in this hydrolysis with alkanols such as 1-pentanol and 1-hexanol.

DESCRIPTION OF THE PREFERRED EMBODIMENTS

Several thousand tons of methionine are produced annually. Chemically, methionine is 2-amino-4-methylthiobutanoic acid. Its empirical formula is $C_5H_{11}NO_2S$ and molecular weight is 149.21. Methionine performs special functions in joint nitrogen and sulfur metabolism, in transmethylation and in nucleic acid synthesis. Because the D and L forms have the same biological activity, the effectiveness of DL-methionine, L-methionine and D-methionine are the same.

Methionine is prepared using the following reaction:

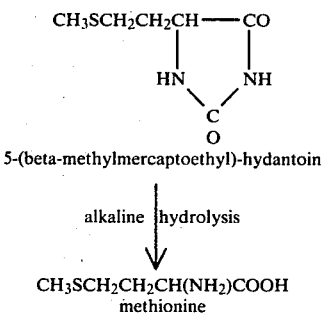

5-(beta-methylmercaptoethyl)-hydantoin alkaline hydrolysis $CH_3SCH_2CH_2CH(NH_2)COOH$
methionine by refluxing an alkaline medium containing one mole of the hydantoin with from about one mole to about eight moles of a metal hydroxide and with from about 500 to about 5000 milliliters of an alkanol having a boiling point of from about 125° C. to about 230° C. at atmospheric pressure, preferably, a water saturated alkanol having a boiling point of from about 125° C. to about 230° C. and thereafter recovering the methionine.

5-(Beta-methylmercaptoethyl)-hydantoin is a well known compound. It can be prepared from 3-methylmercaptopropionaldehyde, ammonium carbonate and potassium cyanide in 50% aqueous ethanol using the Bucherer procedure described by Henze and Long in Jour. Am. Chem. Soc., 63, 1936 (1941).

The reagents employed in the hydrolysis of the hydantoin to methionine may be added separately or may be added as mixtures. For example, the metal hydroxide may be added separately or mixed with the alkanol. Metal hydroxides such as sodium hydroxide, potassium hydroxide and barium hydroxide are preferred.

Any alkanol with a boiling point from about 125° C. to about 230° C. at atmospheric pressure may be used. If desired, mixtures of such alkanols may be used. Useful alkanols include:

2-methyl-1-butanol
3-methyl-1-butanol
1-pentanol
1-hexanol
2-ethyl-1-hexanol
1-decanol
cyclopentanol and
cyclohexanol.

The water saturated alkanol is prepared by saturating the alkanol with excess water at room temperature. If desired, the required amount of water and alkanol can be added to the reaction mixture and the water saturated alcohol prepared in situ.

For a fuller understanding of the nature and advantages of this invention, reference may be made to the following examples. These examples are given merely to illustrate the invention and are not to be construed in a limiting sense. All quantities, proportions and percentages are by weight and all references to temperature are °C. unless otherwise indicated.

EXAMPLE I

This example demonstrates a preparation of methionine from 5-(beta-methylmercaptoethyl)-hydantoin which is within the scope of this invention.

A mixture of 13.1 g of 98% sodium hydroxide pellets (0.32 mole) and 17.4 g (0.10 mole) of 5-(beta-methylmercaptoethyl)-hydantoin in 100 ml of water-saturated n-hexanol was heated to boiling over 25 minutes and refluxed with stirring for 26 minutes, after which the reaction mixture was quenched. The cold reaction mixture was stirred with 75 ml water for ¼ hour, and the aqueous phase was separated. The organic phase (n-hexanol) was washed with four 25 ml portions of water. The combined, filtered, aqueous phases were neutralized to pH of 6 with concentrated hydrochloric acid, stirred at room temperature for the crystallization of methionine, and stored at 5° C. The reaction product was collected, washed with water, and dried to give 3.2 g of methionine, m.p. 268° C. decomposition. The combined mother-liquor and washings were concentrated to about 80 ml during which methionine crystallized. After the mixture had been chilled at 5° C., the reaction product was collected, washed with water, and dried to obtain 3.5 g of methionine, m.p. 268° C. decomposition.

The final mother-liquor and washings were acidified to pH of 1 with concentrated hydrochloric acid and evaporated to dryness in vacuo on a steam bath. The air dried residue was extracted with five 50 ml portions of refluxing methanol. The combined extracts were filtered and concentrated to 25 ml on the steam bath. The hot concentrate was filtered with suction, using two 5 ml portions of hot methanol to wash the separated, inorganic salts. The combined filtrates were again concentrated to 20 ml and filtered hot by gravity, using two 2.5 ml portions of hot methanol as rinsings.

The combined filtrates were treated with pyridine until neutral to Congo red. On cooling, methionine crystallized. After the mixture had been stored at 5° C., the product was collected, washed with methanol, and dried to give 3.9 g of impure methionine, m.p. 213°–220° C. decomposition. The combined yield of methionine represented a yield of 65% of theoretical.

EXAMPLE II

This example demonstrates a preparation of methionine from 5-(beta-methylmercaptoethyl)-hydantoin which is within the scope of this invention.

A mixture of 52.7 g of 96.3% pure barium hydroxide octahydrate (0.16 mole) and 17.4 (0.10 mole) of 5-(beta-methylmercaptoethyl)-hydantoin in 174 ml of water-saturated n-hexanol was heated to boiling with stirring and refluxed for 8 hours in a stainless steel flask.

The reaction mixture was washed out of the stainless steel flask with about 500 ml of water and about 50 ml of methanol. To the reaction mixture was added 9.2 g of ammonium carbonate, and the resulting mixture was stirred at room temperature for thirty minutes and then heated on the steam bath to distill off most of the methanol.

The residual mixture was heated in vacuo on the steam bath to steam distill the n-hexanol, adding water intermittently to keep the water volume essentially constant. The remaining hot mixture was filtered with suction, and the collected barium carbonate was thoroughly washed with hot water.

The combined filtrate and washings were re-filtered and evaporated to dryness in vacuo on the steam bath. The air dried residue was digested on the steam bath with 75 ml of 3A ethanol collected on a filter, washed with methanol, and dried in air at 50° C. to give 16.7 g of pale yellow, sticky solids, m.p. 225°–230° C. decomposition. The reaction product was slurried with 50 ml of isopropyl acetate for 2 hours, collected, washed with three 15 ml portions of isopropyl acetate, and dried for 3 hours at 90°–95° C. to obtain 16.1 g of pale yellow solids, m.p. 225°–230° C. decomposition. Analysis of the reaction product showed it to be 76.23% pure methionine, corresponding to a yield of 82.3% of theoretical.

EXAMPLES III–V

These examples describe methionine preparations employing the procedure given in Example I with the following exceptions. In Example III, 0.32 mole sodium hydroxide was added to the reaction mixture initially; the mixture then heated to reflux temperature over 30 minutes and refluxed for a total of 68 minutes. In Example IV, the procedure used in Example III was followed but the reaction mixture was only refluxed for 45 minutes. In Example V, 150 ml of water saturated 3-methyl-1-butanol instead of 100 ml water saturated 1-hexanol was used and the reaction mixture was refluxed for 24 hours instead of 68 minutes.

|  | Example No. | | |
| --- | --- | --- | --- |
|  | III | IV | V |
| Ingredients |  |  |  |
| hydantoin | 0.1 m | 0.1 m | 0.1 m |
| sodium hydroxide | 0.32 m | 0.32 m | 0.32 m |
| water saturated 1-hexanol | 100 ml | 100 ml |  |
| water saturated 3-methyl-1-butanol |  |  | 150 ml |
| Hydrolysis conditions |  |  |  |
| reflux temperature °C. | 128–136 | 127–134 | 104–110 |
| reflux time | 68 min | 45 min | 24 hours |
| 1st crop | 48.3% | 55.7% | 36.2% |
| mp °C. | 269 dec | 269 dec | 267 dec |
| 2nd crop | 10.7% | 9.4% | 18.1% |
| mp °C. | 237 dec | 263 | 230 dec |
| Total | 59% | 65.1% | 54.3% |

While the invention has been described with reference to certain specific embodiments thereof, it is understood that it is not to be so limited since alterations and changes may be made therein which are within the full and intended scope of the appended claims.

What is claimed is:

1. A process for preparing methionine from 5-(beta-methylmercaptoethyl)-hydantoin comprising hydrolyzing at atmospheric pressure and a temperature of from about 105° C. to about 230° C., one mole of the hydantoin with from about one mole to about eight moles of a metal hydroxide in a medium containing from about 500 to about 5000 milliliters of an alkanol having a boiling point of from about 125° to about 230° C. and thereafter recovering the methionine.

2. The process of claim 1 wherein a water saturated alkanol is present.

3. The process of claim 1 wherein about 1000 to about 2000 milliliters of water saturated alkanol per mole of the hydantoin is present.

4. The process of claim 1 wherein the metal hydroxide is selected from the group consisting of sodium hydroxide, potassium hydroxide and barium hydroxide.

5. The process of claim 1 wherein the alkanol is selected from the group consisting of
2-methyl-1-butanol,
3-methyl-1-butanol,
1-pentanol,
1-hexanol,
2-ethyl-1-hexanol,
1-decanol,
cyclopentanol, and
cyclohexanol.

6. The process of claim 4 wherein the metal hydroxide is sodium hydroxide.

7. The process of claim 4 wherein the metal hydroxide is barium hydroxide.

8. The process of claim 5 wherein the alkanol is 1-hexanol.

9. The process of claim 5 wherein a water saturated alkanol is present.

10. The process of claim 9 wherein water saturated 1-hexanol is present.

* * * * *